(12) United States Patent
Kaplan

(10) Patent No.: US 6,581,773 B2
(45) Date of Patent: Jun. 24, 2003

(54) WEIGHT-SPECIFIC ELIXIR DOSAGE CALCULATOR

(76) Inventor: Brian Kaplan, 19060 SE. Kokomo La., Jupiter, FL (US) 33458

( * ) Notice: Subject to any disclaimer, the term of this patent is extended or adjusted under 35 U.S.C. 154(b) by 41 days.

(21) Appl. No.: 09/919,985

(22) Filed: Jul. 31, 2001

(65) Prior Publication Data

US 2001/0050242 A1 Dec. 13, 2001

Related U.S. Application Data

(63) Continuation-in-part of application No. 09/505,592, filed on Feb. 16, 2000, now Pat. No. 6,276,533.

(51) Int. Cl.$^7$ ............................................. B65D 83/04
(52) U.S. Cl. ..................... 206/534; 206/459.1; 116/321
(58) Field of Search .................. 206/528, 534, 206/540, 459.1, 459.5, 484; 40/310, 312, 490; 116/306, 307, 321, 323; 215/230

(56) References Cited

U.S. PATENT DOCUMENTS

| | | |
|---|---|---|
| 3,151,599 A | 10/1964 | Livingston |
| 3,355,067 A | 11/1967 | Espinal |
| 3,572,282 A | 3/1971 | Tump et al. |
| 3,960,713 A | 6/1976 | Carey |
| 3,996,879 A * | 12/1976 | Walton ........................ 206/534 |
| 4,041,628 A | 8/1977 | Sasson |
| 4,666,051 A | 5/1987 | Trick |
| 4,749,093 A | 6/1988 | Trick |
| 4,753,189 A | 6/1988 | Mastman et al. |
| 4,877,119 A * | 10/1989 | Hosking ...................... 206/534 |
| 4,920,912 A | 5/1990 | Kirkling |
| 4,951,596 A * | 8/1990 | Wallace, Jr. ................. 116/321 |
| 5,011,032 A | 4/1991 | Rollman |
| 5,279,422 A | 1/1994 | Adams |
| 5,358,117 A | 10/1994 | Adams |
| 5,377,614 A | 1/1995 | Glazer |
| 5,607,078 A * | 3/1997 | Nordberg et al. ............. 116/321 |
| 5,979,698 A * | 11/1999 | Deal ............................ 206/534 |
| 6,089,180 A * | 7/2000 | Nichols, Jr. .................. 206/534 |

* cited by examiner

Primary Examiner—Luan K. Bui
(74) Attorney, Agent, or Firm—McHale & Slavin

(57) ABSTRACT

A calculation aid is disclosed forming an integral part of a medication bottle. The calculation aid provides a reference chart for pediatric elixirs to assist in the accurate calculation of the weight-specific dosage for a child. The bottle includes parallel columns of patient's weights and rows of calculated quantity of elixir corresponding to the calculated dose. A movable indicator with an aperture allows selected viewing of the indicia.

13 Claims, 2 Drawing Sheets

WEIGHT-SPECIFIC ELIXIR DOSAGE CALCULATOR

This application is a continuation in part of Ser. No. 09/505,592, filed on Feb. 16, 2000 now U.S. Pat. No. 6,276,533.

FIELD OF THE INVENTION

The present invention relates to improvements in medicine bottles and more specifically, to a weight-specific dosage calculation aid for elixirs to provide a reference source on a medicine bottle for calculating doses of an elixir based upon an individual's weight.

DESCRIPTION OF THE PRIOR ART

Currently, pediatric elixirs such as acetaminophen, ibuprofen and decongestants/cough suppressants are packaged in bottles which have vague and wide ranges of dosing recommendations for children of different weights. For instance, some dosing recommendations on bottles are based on the child's age. However, pediatric elixir dosing is specifically to be based on weight as per the Physician's Desk Reference. This is especially critical in view of the significant variations of weights of children of the same age making age determination not only inaccurate, but most dangerous.

Without a direct reference, even elixirs prescribed by a physician can lead to inappropriately low doses of a medication. For instance, when a child's physician instructs a child's guardian to deliver a certain amount of elixir to a child on a certain date, should the guardian continue to give the child the same amount of medication months later, the dosage will not be correct if the child's weight has changed. A child's weight can change quickly and if the guardian does not inform the physician of the weight change, the dosage will be improper. Continual adjustments in dosing, necessitated by the child's rapidly changing body weight, is important to ensure maximum therapeutic response to a medication. As a physician, it is not uncommon to hear a parent inquire as to why their child's fever has not gone down despite the use of medication prescribed four months earlier. Or more critically, why does my child's fever increase shortly after receiving a dose of the acetaminophen.

Although there currently exist weight-specific dosage calculations presented on charts and pinwheels, they are not readily available to the general public. Even if available, the charts could present a confusing array of dosages that may not be understood by the general consumer. The Physician's Desk Reference may be used for the calculation but such a reference book is not typically purchased or understood by the average consumer.

The use of bottle mounted or integrated indicators are known in the art but have a primary purpose to act as medication or dosage reminders.

U.S. Pat. No. 4,666,051 discloses a bottle located memory aid for use in indicating one in a sequence of predetermined times for dispensing medication.

U.S. Pat. No. 4,749,093 discloses a memory aid for use in reminding patients to take medicine that can accommodate different dosage schedules for the medicine.

U.S. Pat. No. 5,377,614 discloses an indicator showing weekday, date and time for taking a pill or other medicinal dose.

U.S. Pat. Nos. 5,358,117 and 5,279,422 disclose bottle indicators having indicia circumferentially marked around the bottle representing the next time for taking medicine.

U.S. Pat. No. 4,920,912 discloses a time dial which indicates both when medication was last taken and when medication should be taken next.

U.S. Pat. No. 5,011,032 discloses a patient dosage regimen compliance cap which reminds a patient which dose was last take or which dose is yet to be taken and displays the number of medication units to take at each administration.

U.S. Pat. No. 4,753,189 discloses a medicine bottle cap having a dosage indicator to indicate the next dosage time or other information for the user. The indicator is moved incrementally from one location to another to indicate the time for the next dosage, following the removal of medicine from the bottle.

Other dosage indicating closures for medicine bottles have been known and used in the past including: U.S. Pat. Nos. 3,151,599; 3,355,067; 3,572,282; 3,960,713; 4,041,628;

While the prior art is directed to memory aids to remind patients 1) what days to take their prescribed medications, 2) the number of times per day to take the medications, 3) when they took their last dose, 4) when they are to take their next dose, 5) the number of pills to take at each dosing interval, no prior art exists for a calculation aid to determine the exact weight specific dose of an elixir for a patient, of which children require the most specific determination due to their size and ever changing weight.

Thus, what is needed is a weight-specific dosage calculation reference on the elixir container that provides a convenient, user-friendly, immediately accessible way to assure that a child requiring an elixir will attain its maximal therapeutic effects by receiving the exact dose recommended for the child, given the child's weight. Conversely, a container mounted weight-dosage conversion reference will virtually eliminate the occurrence of children receiving inappropriately high dosages for their weight, mistakes which in some cases are potentially toxic or even lethal.

SUMMARY OF THE INVENTION

This invention is a weight-specific dosage calculation reference for use with a medicine bottle. The calculation reference employs narrow apertures on a vertically movable collar allowing a plethora of specific dosing recommendations inscribed on the side of a bottle.

In a preferred embodiment of the invention, there is provided a label mounted reference for a specific elixir's previously calculated doses corresponding to specific pediatric patient weights. If the patient's weight falls between the specific weights on the label, the specific dosage may be interpolated or calculated.

In an alternative embodiment, provided is a bottle mounted reference for a specific elixir's previously calculated doses corresponding to specific pediatric patient weights.

Thus an objective of the invention is to provide accurate, calculated information as an integral part of the elixir bottle.

Another objective of the invention is to eliminate the need for reference books, pinwheels, or the like disjointed materials that are used for calculation but do not form an integral portion of the bottle.

Another objective of the invention is to provide a format available to the physician for providing specific dosages that need to be modified according to the weight of the child.

Still another objective of the invention is to provide a specific dosage calculator that has application for adults, children, and pets.

Another objective of the invention is to reduce the exposure of an inappropriately high dose of medication due to vague and wide ranges currently provided on most elixir bottles designed to address the average child's weight at a particular age.

Another objective of the invention is to provide an elixir bottle with a simple scale and a vertically movable indicator to visually expose a proper dosage of elixir for a particular patient's weight.

Yet still another objective of the invention is to provide a device that allows for calculating the proper dose of medication as the dosage pertains to the weight of an adult, child or pet.

It is a further objective of this invention to promote proper dosing to maximize the therapeutic effects of a medication.

Other objectives and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

DETAILED DESCRIPTION

Although the invention will be described in terms of a specific embodiment, it will be readily apparent to those skilled in this art that various modifications, rearrangements and substitutions can be made without departing from the spirit of the invention. The scope of the invention is defined by the claims appended hereto.

Figure 1:
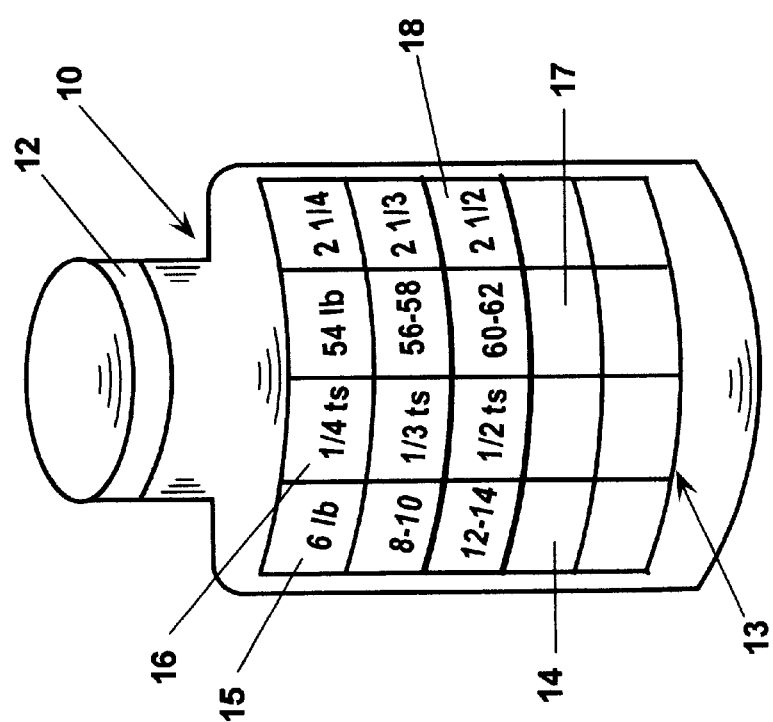
FIG. 1 is a perspective of an elixir container illustrating the spread sheet portion of the inner label.

Now referring to FIG. 1, set forth is the preferred embodiment of the instant invention in which a calculation aid is used with medication bottle 10 having an open top and a closure or bottle cap 12 and a label 13 which includes an integral calculation reference chart. In the most basic form, the label 13 is made from two components carrying indicia, an inner component 14 used for descriptive information concerning the contents of the bottle, manufacturer, etc. and a spread sheet with different weights in one set of fields 15 paired with optimal dosing amounts in adjoining fields 16.

The outer component or sleeve 17 is slidable on the inner sleeve and has apertures for viewing of the calculation reference. Preferably the closure cap 12 is tamper-proof.

The inner component 14 includes inscribed indicia set forth in a number of parallel columns. One column 15 contains various children weights in pounds in increasing amounts, a contiguous row 16 contains the previously calculated optimal dose appropriate for a specific weight in liquid measure. A second column 17 continues the weights in increasing numbers and a contiguous row 18 gives the dosage in liquid measure. There may be more or less rows of indicia.

As shown in FIG. 1, the printed weights and comparable dosing amounts are oriented to be read vertically about the longitudinal axis of the bottle. An alternative form of presentation would present the information in the fields at a 90 degree angle. The weights may be in increasing order or decreasing order. The weights and liquid measures may be metric or English or both or combinations thereof. Further, the inner label may be omitted and the information may be embossed on the bottle 10.

Figure 2:
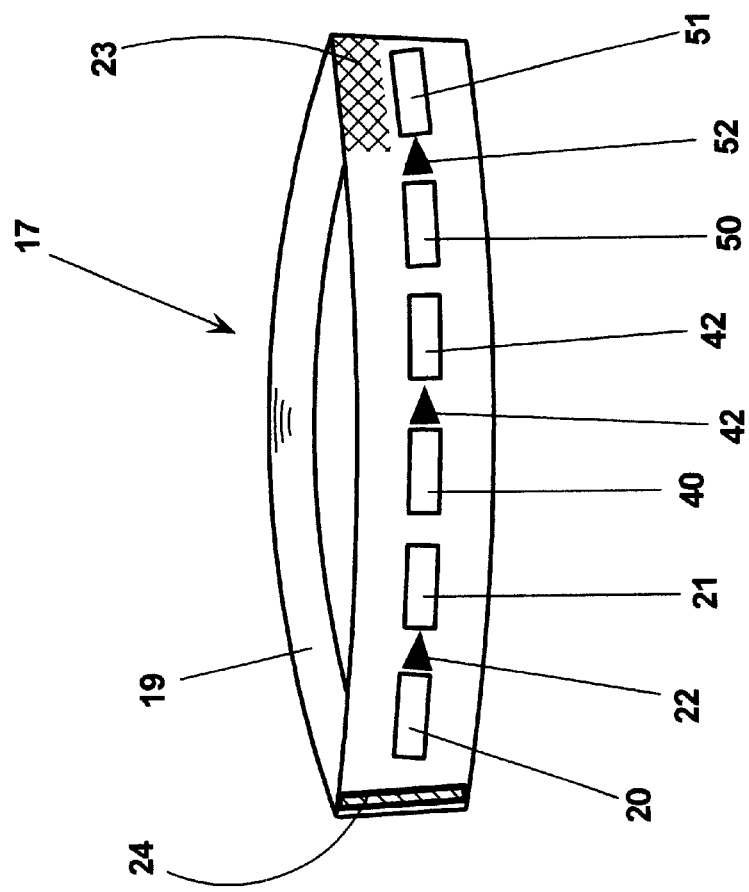
FIG. 2 is a perspective of the outer member of the label showing apertures.

The outer member 17 is a frictional collar 19, preferably of a plastic material, which has a row of apertures, as shown in FIG. 2. The collar 19 is formed in a tubular ring shape with a diameter approximating the diameter of the bottle to which it is applied. The width of the outer member is approximately the same as the height of the indicia in the rows on the chart. As shown in FIG. 2, there are two apertures 20 and 21 with one indicator 22, in the form of an arrow-heads formed in contrasting colors. The indicator 22 links the pair of apertures and directs the user to read the information appearing in the apertures together. In FIG. 2 there are three pair of apertures shown, apertures 20 and 21 are linked by indicator 22, apertures 40 and 41 are linked by indicator 42, and apertures 50 and 51 are linked by indicator 52. There may be one pair, two pair or more pairs of apertures linked by indicators. The indicators expose the contiguous rows of dosages as the collar is moved vertically along the columns of weights. The collar may be made without apertures and the circumferential edge of the collar acts as an indicator between rows.

The ring may be slightly elastic to permit assembly and to prevent inadvertent movement, to mis-align the apertures and indicia, without undue binding between the inner label 13 and the outer ring 17. The outer member may include structure to increase the adhesion between the user's fingers and the outer ring 17. This structure could include areas of roughened or cross-hatched surface 23 on the outer ring. Alternatively, the outer ring may have a raised ridge 24. As shown, both the roughened area and the ridge are present.

The calculation aid, as it is weight specific and not patient specific, can be mass distributed on over-the-counter medications as opposed to requiring a pharmacist to set and permanently fix or secure it to denote a specific patient's needs.

The calculation reference functions by the sliding movement of the plastic collar 19. An individual advances the collar to display the child's weight in the first aperture 20. In turn, the dosage in appropriate units of measure is displayed in the linked aperture as shown by the indicator 21.

Figure 4:
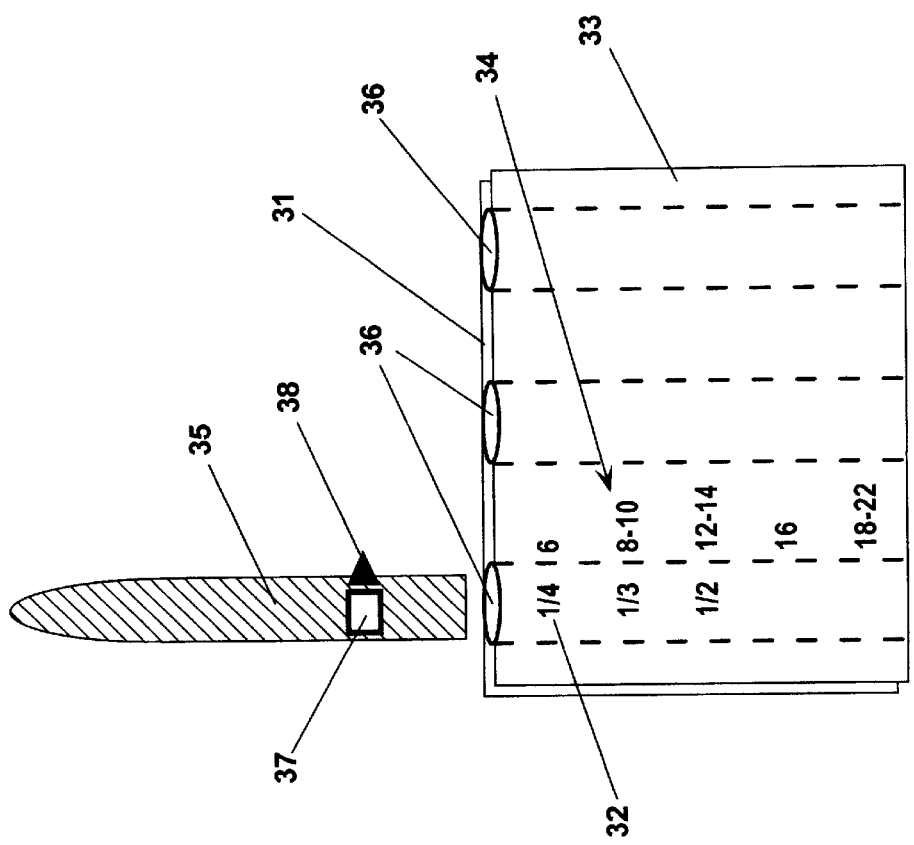
FIG. 4 is an exploded perspective of the calculation aid of FIG. 3.
Figure 3:
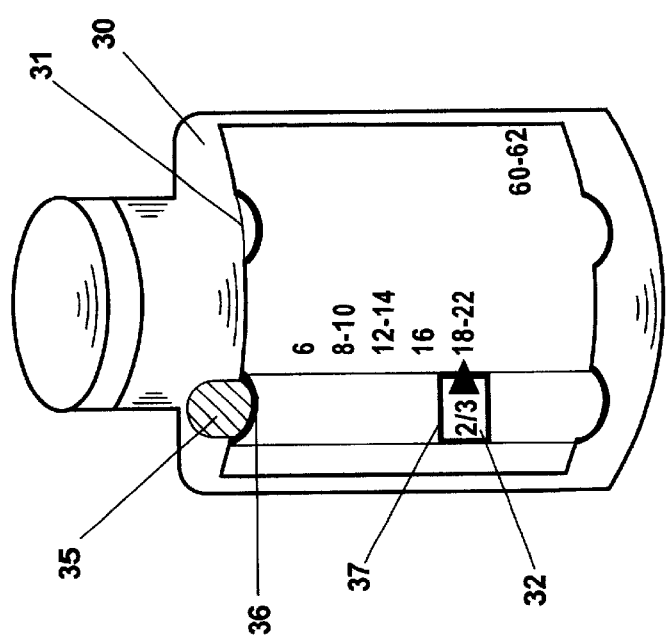
FIG. 3 is a perspective of another modification of the vertical scale.

Referring to FIGS. 3 and 4, an elixir container 30 has an inner label 31 containing dosage indicia 32 in particular units of measure. The dosage indicia is spatially arranged on the inner member in relation to the appropriate weight of the patient for that dosage. An outer member 33 has a column 34 of specific weights that would cause the amount of dosage to change. The outer member 33 is connected to the inner member 31, except in the area of the column 34. Between the inner and outer member there is a movable tab 35 vertically slidable in the disconnected tube 36 the column. The tab 35 may be translucent or solid. The outer member 33 is transparent in the area of the tube 36. The tab has an aperture 37 and an indicator 38 used to indicate the patient's weight. When the indicator 38 is set on the patient's weight, an aperture 37 on the tab 35 visually frames the appropriate dosage located on the inner member 31. Of course, the indicia may be reversed with the dosage on the tab and the weight on the inner member. The tab may be transparent also, with a line as an indicator. As shown, the tab moves vertically in relation to the longitudinal axis of the bottle. In FIG. 4 a series of tubes 36 permits a greater range of weights and dosages.

In another embodiment, both the dosage amounts and the weights may be located on the inner member. The outer member is entirely transparent and attached to the inner member between associated columns of weights and dosages. The tab slides in the tubular openings to expose the dosage associated with a particular weight.

The calculation aid employs indicia directed to a specific medication of a specific concentration. This strict condition comes with the understanding that different weight dose conversion factors are required: a) when the same medication is manufactured at a different concentration, b) when relating to different medications altogether. As a general precaution, the medication name and concentration is to be inscribed upon the container, so that its user can verify that the inscribed calculations do, in fact, relate to the medication within the bottle to which it is attached.

What I claim is:

1. A dosage calculation aid for a medicine bottle, said dosage calculation aid comprising a scale with vertical columns and horizontal rows, said columns including a range of patient's weights with associated rows containing dosage amounts, said dosage amounts precalculated as optimal dosage for the associated weight and an indicator, said indicator overlying said scale and exposing said associated row, said indicator movable along said columns to expose a selected weight and said dosage amount precalculated as optimal for said weight.

2. A dosage calculation aid according to claim 1 wherein said scale is contained on a label, said label affixed to said medicine bottle and said indicator is a tubular sleeve frictionally engaging said medicine bottle.

3. A dosage calculation aid according to claim 2 wherein said tubular sleeve has a row of at least two apertures, said apertures expose a patient's weight and said associated row of said optimal dosage for said weight.

4. A dosage calculation aid according to claim 1 wherein said scale is embossed in said medicine bottle.

5. A dosage calculation aid according to claim 2 wherein said indicator is a tubular sleeve frictionally engaging said medicine bottle.

6. A dosage calculation aid according to claim 2 wherein said columns are oriented along the longitudinal axis of said medicine bottle and said indicator slides vertically on said scale.

7. A dosage calculation aid according to claim 5 wherein said columns are oriented along the longitudinal axis of said medicine bottle and said indicator slides vertically on said scale.

8. A dosage calculation aid for a medicine bottle, said dosage calculation aid comprising an inner member and an outer member, said inner member having columns of dosage amounts, said outer member having columns of weights, said columns of dosage amounts associated in rows with said columns of weights and a tab slidably disposed between said inner member and said outer members, said tab having an indicator thereon, whereby when said tab is slid along said columns a specific dosage amount is indicated for a particular weight.

9. A dosage calculation aid of claim 8 wherein said outer member is transparent at least between said columns of weights.

10. A calculation aid according to claim 9 wherein said inner member and said outer member are attached between said columns of weights.

11. A calculation aid according to claim 8 including wherein said indicator includes an aperture, said aperture exposing said dosage amount for a particular weight as said tab is slid along said column of weights.

12. A dosage calculation aid of claim 8 wherein said inner member has columns of weights and said outer member has columns of dosages.

13. A dosage calculation aid of claim 8 wherein said columns of weights and said columns of dosages are located on said inner member.

* * * * *